United States Patent
Del Rio et al.

[19]

[11] Patent Number: 5,876,405
[45] Date of Patent: Mar. 2, 1999

[54] PERFORATOR

[75] Inventors: Eddy H. Del Rio, Royal Palm Beach; William E. Anspach, III, Stuart, both of Fla.

[73] Assignee: The Anspach Effort, Inc., Palm Beach Gardens, Fla.

[21] Appl. No.: 932,016

[22] Filed: Sep. 17, 1997

[51] Int. Cl.⁶ .................................................. A61B 17/56
[52] U.S. Cl. .................................................................. 606/80
[58] Field of Search ............................... 606/80, 79, 82, 606/84, 85, 86, 96, 97, 98

[56] References Cited

U.S. PATENT DOCUMENTS

| | | |
|---|---|---|
| 2,504,075 | 4/1950 | Trephine . |
| 2,525,669 | 10/1950 | Hainault . |
| 2,842,131 | 7/1958 | Smith . |
| 3,797,497 | 3/1974 | Crim et al. . |
| 4,319,577 | 3/1982 | Bofinger et al. . |
| 4,362,161 | 12/1982 | Reimels et al. . |
| 4,456,010 | 6/1984 | Reimels et al. . |
| 4,600,006 | 7/1986 | Baker . |
| 4,699,550 | 10/1987 | Baker . |
| 4,803,982 | 2/1989 | Baker . |
| 4,830,001 | 5/1989 | Walus . |
| 4,884,571 | 12/1989 | Baker . |
| 4,951,690 | 8/1990 | Baker . |
| 5,007,911 | 4/1991 | Baker . |
| 5,135,532 | 8/1992 | Baker . |
| 5,330,480 | 7/1994 | Meloul et al. . |

*Primary Examiner*—Guy V. Tucker
*Attorney, Agent, or Firm*—Norman Friedland

[57] ABSTRACT

The drill bit for drilling a hole in bone structure is made to inherently prevent cutting when the resistive force is removed by providing an annular wall with a cutting edge formed on the bottom edge and lying in a plane that is in the circumferential plane of the annular wall and providing a shield in the same plane and disposed adjacent to the cutting edge that is automatically displaced when a resistive load is applied and automatically returns to shield the cutting edge when the resistive load ceases. In one embodiment the wall of the annular wall is judiciously slotted to provide the automatic movement of the shield and in another embodiment the shield is spring load to be displaced and returned to its original position. The perforator of this invention includes safety mechanism that prevents penetration of the perforator when the drill bit has completed the cutting operation and the resistive load is removed. The perforator cuts the hole by an annular slot leaving a plug of the bone structure that is removed and returned to the original hole for re-filling the hole which aids in the healing process. A clutch may be provided that decouples the drill bit from the drive motor upon sensing a void in the drill passage during the drilling operation.

39 Claims, 15 Drawing Sheets

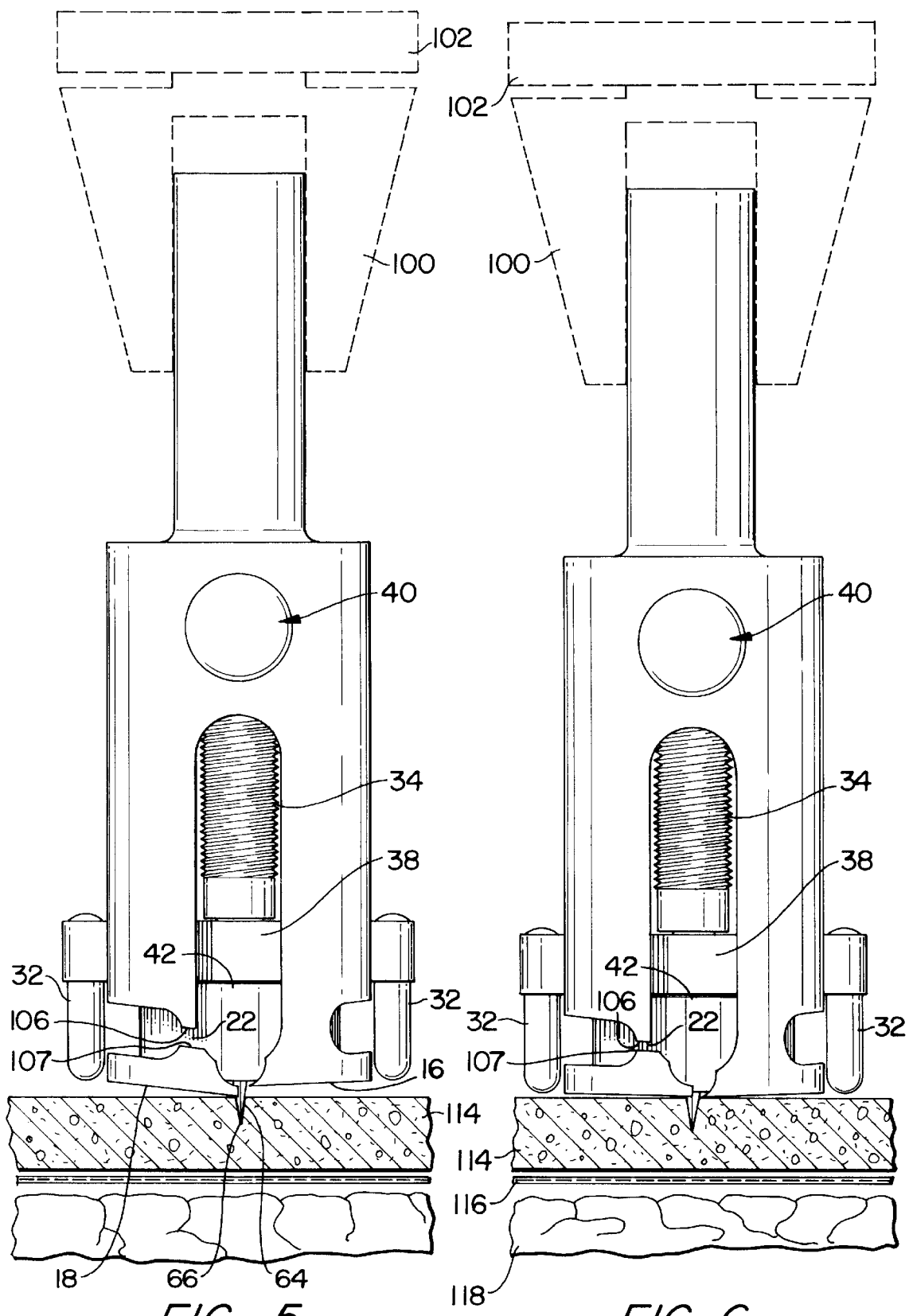

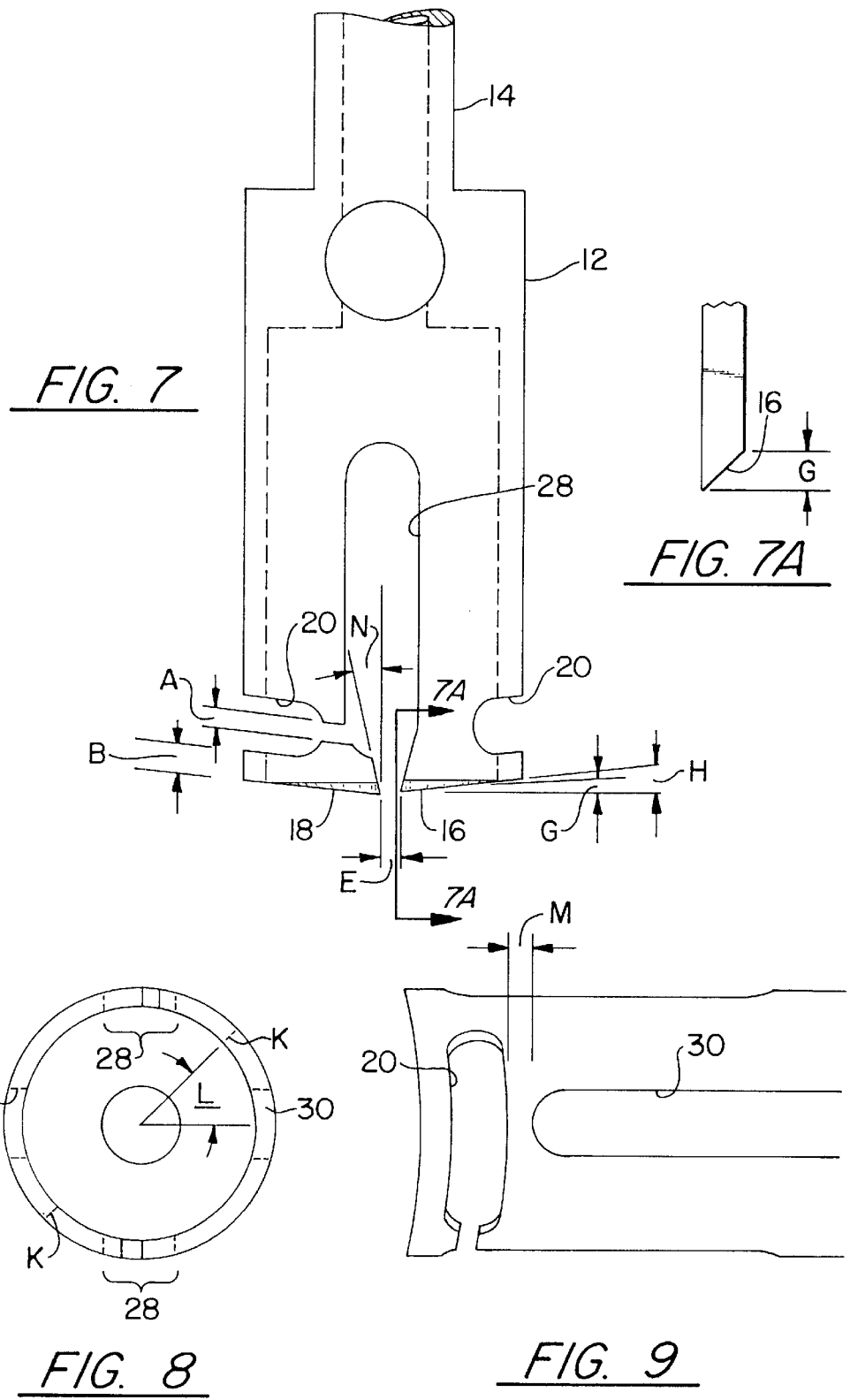

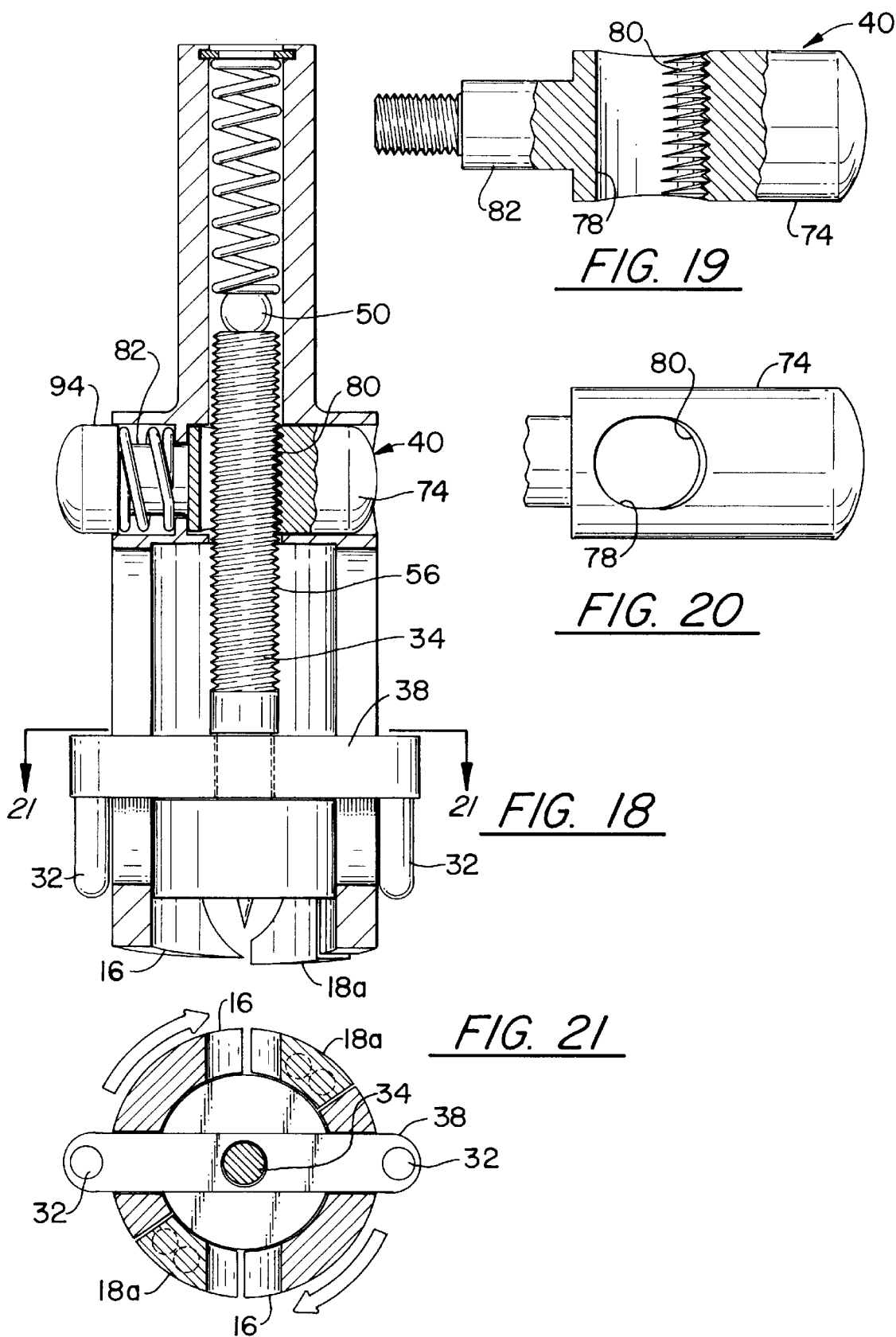

PERFORATOR

TECHNICAL FIELD

This invention relates to surgical drills or perforators for use on human and animal bones and skulls and particularly to the type that automatically stops drilling upon reaching a certain penetration threshold.

BACKGROUND ART

As is well known in the surgical instrument technology, trepans or cranial drills or perforators that serve to drill a hole in the skull must stop instantly upon reaching a certain depth. It is abundantly important that the drilling does not go beyond the depth of the skull and penetrate through the dura underlying the bone structure and/or the brain underlying the dura. There are a plethora of prior art patents that disclose cranial drill instruments that are intended to provide this function and for the most part these instruments utilize a concentric type of perforator or cranial drill that include an inner bit (front drill head assembly) and an outer bit (trailing outer drill). The inner bit senses the load occasioned by the operator applying pressure to the drill which is forced against the bone structure and when the inner bit no longer feels the resistive force the drilling stops by virtue of a clutching type of mechanism that responds to the axial position of the inner drill bit. Patents that exemplify this type of drill or perforator are U.S. Pat. No. 4,600,006 granted to Baker on Jul. 15, 1986 entitled "Cranial Perforator", U.S. Pat. No. 5,007,911 granted to Baker on Apr. 16, 1991, entitled "Drill Head Assembly For Cranial Perforators", U.S. Pat. No. 4,884,571 granted to Baker on Dec. 5, 1989, entitled "Cranial Perforator With Reentrant Cutting Segment", U.S. Pat. No. 4,699,550 granted to Baker on Oct. 13, 1987 entitled "Cranial Perforator", U.S. Pat. No. 5,330,480 granted to Meloul et al on Jul. 19, 1994 entitled "Surgical Drill", U.S. Pat. No. 4,951,690 granted to Baker on Aug. 28, 1990 entitled "Method Of Drilling Through A Bone Structure", U.S. Pat. No. 4,803,982 granted to Baker on Feb. 14, 1989 entitled "Cranial Perforator", U.S. Pat. No. 4,362,161 granted to Reimels et al on Dec. 7, 1982 entitled "Cranial Drill", U.S. Pat. No. 4,456,010 granted to Reimels et al on Jun. 26, 1984 entitled "Cranial Drill", and U.S. Pat. No. 4,830,001 granted to Walus on May 16, 1989 entitled "Assembly Sleeve For Cranial Drill".

In these types of instruments noted in the above-referred to patents, the drill bit applies motion to the clutch in order to bring the drill to an eventual stop. This occurs when the inner bit no longer feels the resistive force. Typically the instrument utilizes a pin and slot-type spring biased clutch that links the drill body and drill member together. Then the drill is placed against the bone structure with a force sufficient to overcome the spring bias, the clutch will engage and the driver, drill member and drill body will rotate together. The counterbore on the drill body provides a support for the drill mechanism so that the drill member may release when it penetrates the bone structure without having the remainder of the drill move in the direction toward the cranial cavity. Obviously, the clutch mechanism must displace a certain axial distance before the drill comes to a complete stop. In certain instances, the depth of penetration of the drill owing to this axial distance may present a problem.

An important aspect of this invention is that it eliminates the clutch mechanism of the type that is commercially available and shown in the prior art patents listed above. This invention provides means inherent in the perforator that immediately stops the penetration when the drill bit no longer feels a resistive force. In the perforator of the present invention the drilling forms an annular groove cut into the bone structure such that a portion of the bone in the form of a core or plug remains intact whereby the plug can be reused to partially fill that same hole that was previously drilled. This, obviously, has medical benefits in the closure of the hole in the bone structure and helps in the recovery process of the patient as well.

In the present invention the perforator or drill bit will automatically stop cutting (rotation is stopped when the operator deactivates the drill motor) when the load on the drill bit or perforator is removed. The perforator is cylindrical in shape defining a torroidal bottom edge much like the shape of a cup. The cutting edge is configured within the circumference of the bottom edge and lies in the circumference and facing the next adjacent circumferential portion which serves as a shield. The shield is spring loaded to deflect axially upwardly when forced against a resistive force exposing the edge of the cutting edge to define the cutting position. When the resistive force is eliminated the shield automatically returns to the original position to shield the cutting edge into the non-cutting position.

The invention contemplates using a stop pin assembly that rotates with the drill bit of the perforator and displaces the same distance of the drill bit so that the stop pins remain a constant distance away from the surface of the exterior of the bone structure being drilled during the drilling operation. In other words, if the prongs are set to be spaced say, 0.3 millimeter (mil), the gap between the end of the stop pins and the bone structure will remain this exact distance from the start of the drilling operation until the end of the drilling operation and only additional force exerted on the perforator by the operator will cause the perforator to move axially. The additional axial movement of the perforator will cause the stop pins to move until it penetrates the 0.3 mil gap and come into contact with the bone structure. This will limit penetration of the drill bit of the perforator beyond the cranial drilled hole which is well within safe distance from contacting the dura. This safety feature will assure that the perforator will not be displaced more than the 0.3 mil setting once the resistive force is removed from the drill bit. Obviously, the stop pins support assembly is merely a carry-on to assure that the surgeon doesn't inadvertently injure the dura in a cranial operation by exerting more force than is required to accomplish the drilling. In other types of operations where the drilling is not as exacting and penetration threshold need not be considered, the drill of this invention would have utility without the safety features. Obviously the gap setting of the stop pins can be predetermined as will be explained in connection with the description of the invention that is to follow. As is apparent from the foregoing, the stop pin feature and the ease of drilling with the present invention overcomes some of the resistance to use perforators as expressed by surgeons who are not confident of being able to stop the penetration in time to avoid injury to the dura when using the prior art perforators.

While the invention can be made into a reusable instrument, it would probably have more appeal in certain areas of the intended use of the instrument to be made as a throw-a-way instrument. In either case, the invention is characterized as being relatively inexpensive to make and easy to operate. As will be detailed in the description to follow two embodiments will be disclosed. The first embodiment represents the second design that included a minimum number of components. The second embodiment represents the first design which included many more components than is disclosed in the first embodiment. It will be appreciated by one skilled in the art that either of the embodiments have utility and that each perform the same functions and illustrate that a number of embodiments can be made without departing from the scope of this invention.

In actual testing of the two embodiments of the present invention it was observed by the operators that in drilling the bone structure of a skull, less force was needed by the operator than was required in comparison to the force required when a commercially available perforator of the type described in some of the above reference patents. It was also observed that when the drill bit stopped its cutting the stoppage was so exacting that an extremely thin partial sliver of the bone structure at the bottom of the plug that extending the width of the annular channel drilled by the perforator remained attached to the bone plug. This meant that the automatic stoppage of the cutting by the drill bit occurred before the bottom end of the perforator went beyond the bottom surface of the bone structure. To eliminate the sliver from occurring the cutting edge of the drill bit can be modified to include a contour on the side face of the cutting edge. The side face of the drill bit is the outer circumferential surface.

In certain applications, it is desirable to stop rotation of the drill bit at some point in the drilling operation. This is particularly the circumstance where the bone structure is such that the top surface of the bone is configured differently than the bottom surface and the topography is drastically different. This obviously changes the thickness of the bone in these locations resulting in large transitions of the thickness of the bone structure. In such circumstances, a portion of the drill bit will evidence a void while the remaining portion of the drill bit is in contact with bone structure. Under such circumstances, it may be desirable in ceasing the drilling operation. This invention contemplates utilizing a clutching mechanism that senses the void and declutches the drill bit from the drill motor to stop rotation of the drill bit and hence, cease the drilling operation.

SUMMARY OF THE INVENTION

An object of this invention is to provide an improved perforator.

A feature of this invention is to provide a perforator that eliminates the heretofore known clutching mechanisms and inherently stops when the perforator attains the desired threshold of the depth of the hole. The drill bit of the perforator is cylindrical and torroidal in shape configured similarly to a cup and the cutting edge is formed on the bottom edge and lies in the circumferential plane next to a shield also lying in the circumferential plane. The shield is movable and is either made from resilient material or spring loaded so that it is automatically displaced when forced against the bone structure. As long as there is a resistive force, the shield will be displaced and this small axial displacement exposes the cutting edge when in the drilling mode. When the resistive load is removed, the shield returns to its original position and covers the cutting edge to prevent further drilling and hence penetration.

Another feature of this invention is that the drilling of the perforator defines an annular groove that leaves a core or plug of the bone structure whose diameter is equal to the inner diameter of the perforator. This plug is reusable to partially fill the drilled hole.

Another feature of this invention is that the perforator is made of a minimum number of components and the drill bit in one embodiment is a single integral unit having the cutting edge and shield integrally formed on the base or bottom of the drill bit. Judiciously placed discrete slots in the drill bit allow limited movement of the shield and defines the limit of the depth of the cutting edge. The cutting edge is formed by a machining operation by judicious and discrete cuts and slots. The drill bit is made from a highly resilient surgical metallic or plastic material to allow the shield to be deflected the distance of the gap and return to the original non-cutting position when no force is applied and to obtain a sharp cutting edge. In another embodiment the shield is a separate component that is secured adjacent the cutting edge and spring loaded to displace from the cutting edge to allow for cutting during the drilling operation.

This invention also contemplates a safety mechanism that prevents the perforator from penetrating a predetermined distance after the drilling operation reaches its threshold depth of the drilled cut. The perforator includes a threaded screw that is spring loaded and affixed to the center of the base and is held in the secured position by a latch mechanism that is releaseably secured to the threaded screw. A stop pin bridge/stop pins element is affixed to a shank portion of the threaded screw and rotates with the drill bit and relative to the screw, but translates longitudinally with the drill bit. Since the screw is operatively connected to the latch and mimic the depth of cut, the stop pins remain spaced a minuscule distance from the exterior of the bone being cut and the drill bit cannot be moved more than this preset distance before bearing against the exterior of the bone structure, thus preventing the perforator from being inserted beyond the bottom surface of the bone structure.

At the outset and prior to the operation of the drill bit, it is packaged in the deployed position. The surgeon merely attaches the drill bit to the drill motor and begins the cutting. The triangular shaped guide pin at the end of the threaded screw penetrates into the bone structure and when the bottom surface of the center driver bears against the bone structure the guide pin and center driver hold the screw from rotating while the drill bit is performing the cutting. As soon as the resistive force is removed the shield returns to its original position and the cutting stops and the latch mechanism holds the screw in the retracted position. In instances where the drill bit is reused it is necessary to deploy the threaded screw to begin the cutting operation. Displacement of the latch deploys the threaded screw to position itself so that it can be aligned against the surface of the skull or bone structure and the operation is repeated.

Another feature of this invention is that the perforator is easy to operate and fits into any standard drill motor with a suitable chuck, such as a Jacob chuck, and is characterized as being inexpensive to make and relatively easy to assemble and operate. And, of importance, the perforator of this invention creates confidence in the surgeon that the drill can never penetrate more than the preselected gap dictated by the stop pins and hence, avoiding the possibility of contacting the dura.

Another feature of this invention is to provide an option to the drill bit a clutch mechanism that automatically stops the rotation of the drill bit and hence, the drilling operation, upon the shield sensing a void of bone structure in the course of the drilling operation.

The foregoing and other features of the present invention will become more apparent from the following description and accompanying drawings.

BRIEF DESCRIPTION OF DRAWINGS

FIG. 5 is an elevated view illustrating the shield axially extending below the cutting edge of the drill bit and with the guide pin in the piercing position;

FIG. 6 is an elevated view identical to FIG. 5 with the shield being displaced and the cutting edge approaching the cutting position;

FIG. 7 is a view in elevation illustrating dimensions of the drill bit to obtain the operability of this invention and illustrating the bevelled face on the cutting edge to eliminate the sliver on the bone plug from forming;

FIG. 7A is an enlarged view of the cutting edge of the drill bit taken along lines 7A—7A;

FIG. 8 is a plan bottom view also illustrating certain dimensions;

FIG. 9 is a partial view in elevation of the right side of the view in FIG. 8;

FIG. 18 is a view partly in section and partly in elevation showing the details of the second embodiment of the present invention;

FIG. 19 is a view partly in section and partly in elevation illustrating the latching mechanism;

FIG. 20 is a partial plan view of the latching mechanism;

FIG. 21 is a sectional view taken along the lines 21—21 of FIG. 20 illustrating the attachment for the stop pins;

DETAILED DESCRIPTION OF THE PREFERRED EMBODIMENT

Figure 1:
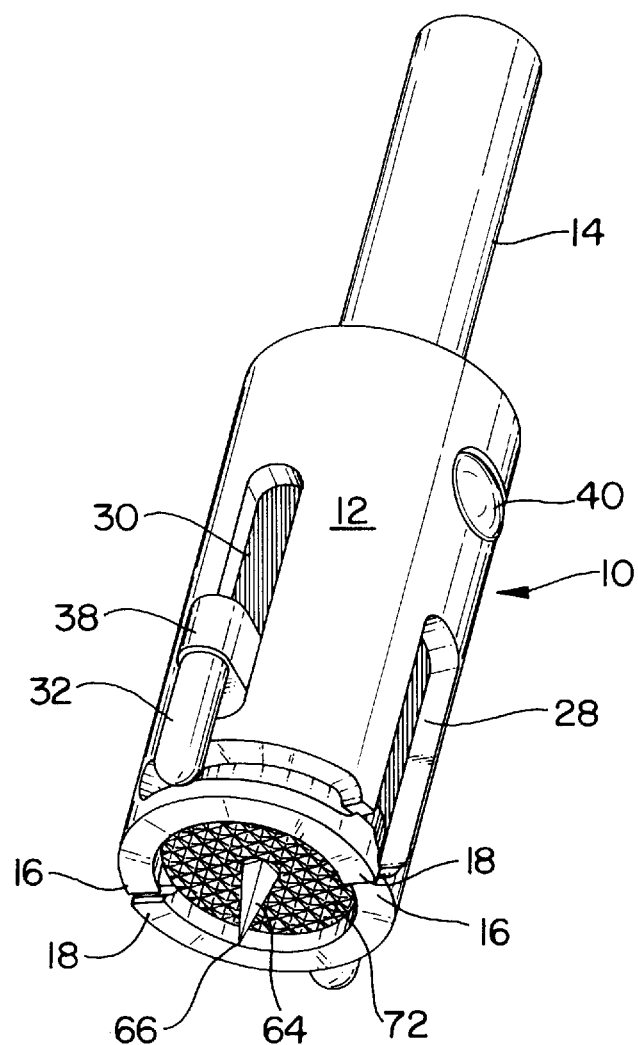
FIG. 1 is an elevated view in perspective showing the perforator of this invention.

While the preferred embodiments of this invention are being described as cranial drills or perforators, it is to be understood that the drill of this invention has utility for drilling holes in any type of bone structure for both human and animal patients.

The invention is best understood by referring to FIGS. 1 through 9 which shows the preferred embodiment of this invention comprising a perforator generally illustrated by reference numeral 10 having a drill bit portion 12 (drill bit) configured like a sleeve or cup such that the hollow cylindrical wall includes a bottom surface. A shaft 14 extending from the top portion of the cylindrical wall defining the drill bit portion 12. The shaft 14 is sized to fit into commercially available chucks that are utilized with various commercially available drill motors that operate say, in the 800 revolution per minute range. The drill bit portion adjacent the bottom edge of the cylindrical wall is vertically and horizontally slotted adjacent the cutting edge 16 and shield 18 in order to obtain the flexibility and cutting and shielding characteristics required by this invention as will be described immediately below. It being noted that the cutting edge 16 lies in a circumferential plane of the cylindrical wall and the shield 18 is in the same plane so that when the resistive force is applied the shield becomes displaced to uncover the cutting edge and when the resistive force is removed the shield automatically and instantly returns to its original position to prevent further cutting.

Because the drill bit is made from a single piece and it requires automatic flexing, proper cutting edge sizing and a given relationship of the shield to the cutting surface, FIGS. 7 through 10 have been included to give certain dimensions that have proven to be satisfactory in one particular size of the perforator, noting that the perforator can be made in different sizes to accommodate different sized drilled holes. The widths of the relatively horizontal slots 20 are dimensioned to say 0.090 inch and are reduced at the junction adjacent to the end of the shield 18 to say 0.030 inch (dimension A). The horizontal slot 20 is spaced say 0.042 inch (dimension B) from the bottom surface of shield 18 and the bottom surface is slightly beveled to say 7 degrees (°) [dimension C]. The wall thickness at the gap 22 of shield 18 is say 0.078 inch (dimension D). The radius at the end 24 of the shield 18 is say, 0.045 (dimension R) which allows for the machining of a sharp edge 26 of the cutting edge 16. The space between the edge of shield 18 and cutting edge 26 is say 0.032 inch (dimension E) and the reference base of the bevelled bottom surface of the cutting edge 16 is say, 2° [dimension F]. The angle between the edges of the shield 18 and sharp edge 26 is say, 15° (dimension N). The width of vertical slot 28 is say, 0.140 inch and extends adjacent to the radius R. To obtain the correct cutting edge 26 and having sufficient relief in the cutting process the bottom of the cutting edge adjacent the sharp edge 26 is say, 5° (dimension G) and a short distance spaced from the sharp edge 26, the angle is increased to say, 7° relative to the base line (dimension H). The bottom of the cutting edge 16 is axially spaced 0.020 inch from the bottom of the shield 18 (dimension J). Obviously, the above dimensions are strictly intended to describe one perforator that has been built and tested successfully. Obviously, as one skilled in this art will appreciate other dimensions can be utilized depending on the size of the unit and the material selected.

The vertical slots 30 (FIG. 9) which are diametrically disposed on the drill bit 12 serve to provide a rotary drive and a guide for the stop pins 32. The end of slot 30 is spaced a distance say, 0.023 inch (dimension M). FIG. 8 shows the relative position of the cutting edge 26, the shield 28, the slots 28 and 30 and the length of slots 20 represented by the dash lines K which is at radius of say 45° (dimension L). Of importance in this design of the perforator is that the shield must automatically return to its initial position immediately upon the removal of the resistive load (the displacement is determined by gap A), the cutting edge is capable of being machined directly into the drill bit, the cutting of the perforator is in one direction and the stop pins 32 automatically mimic the advance of the drill bit into the cranial structure and are pre-adjusted to extend a given distance above the surface of the bone structure being drilled throughout the drilling operation. While in the preferred embodiment a pair of diametrically disposed shields and cutting edges are disclosed, the number of shields and cutting edges are not intended to limit the scope of this invention.

As noted in FIGS. 2 through 6 the perforator 10 consists of the unitary drill bit 12, shaft 14, the screw 34, the stop pins 32 supported in stop bridge 38, the latching mechanism generally illustrated by reference numeral 40 and center driver 42. The drill bit 12 is generally configured similar to a cylindrically shaped cup with the central portion 43 hollowed out, the bottom is open and the top 44 is closed. Shaft 14 includes a central straight-through bore 46 that extends into the central hollow portion 43 for receiving the screw member 34 which is spring loaded in the downward direction by coil spring 48. The ball seat 50 disposed between the end of the screw 34 and the spring 48 assure that the screw is displaced in an axially aligned position. Coil spring 48 is grounded at the top by the retaining split ring that fits into an annular groove 52 formed on the internal diameter of shaft 14. The larger diameter portion 56 of screw 34 is threaded from the top to near the reduced diameter portion 58. The un-threaded shank portion 60 and the shoulder 62 formed at the junction of the two different diameter portions serve to accommodate the stop bridge 38 for reasons that will be described herein below. The bottom end 64 of screw 34 is tapered into several facets that fair into a centrally disposed sharp guide pin 66 that is in coincidence with the central axis of the drill bit. The screw 34 is retained in the drill bit by the center driver 42 which is internally threaded in the central bore 68 and in turn, threaded to the threads 70. As noted from FIG. 2 the bottom surface 72 of center driver 42 is knurled into a diamond shaped sharp pointed surface. The sharp tip 66 of the guide pin 64 with the discrete facet shape and the bottom knurled surface 72 are designed to provide a friction surface and holder for the screw to assure that the screw does not rotate with the drill bit. The drill bit rotates relative to the screw as the drill penetrates into the bone structure. Hence, when the screw is in the operating position the tip 66 of the guide pin 64 will penetrate into the bone structure and the bottom surface 72 will bear against the exterior of the bone structure allowing the facets and friction to prevent the screw from rotating.

Figure 2:
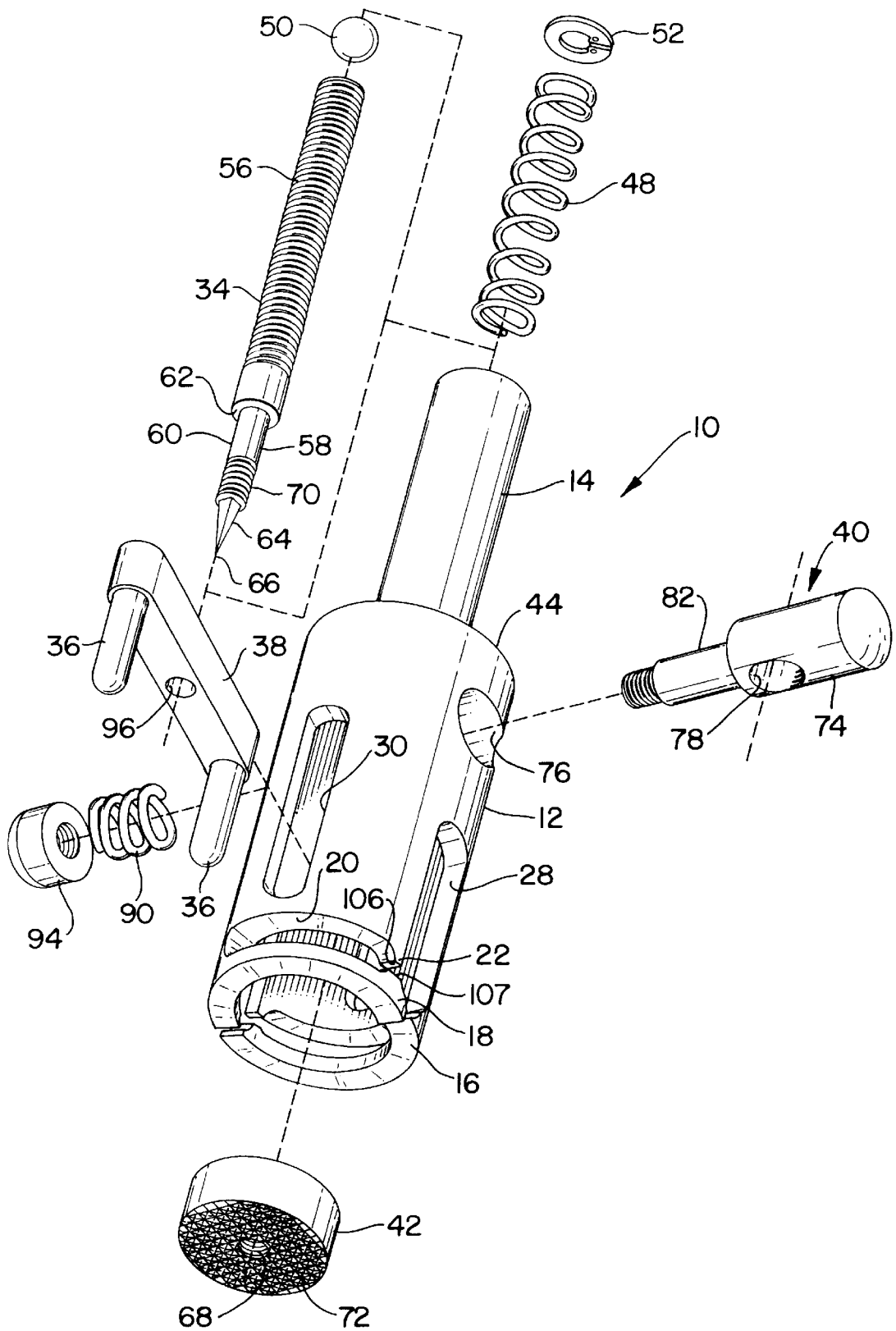
FIG. 2 is an exploded view of the perforator depicted in FIG. 1.
Figure 3:
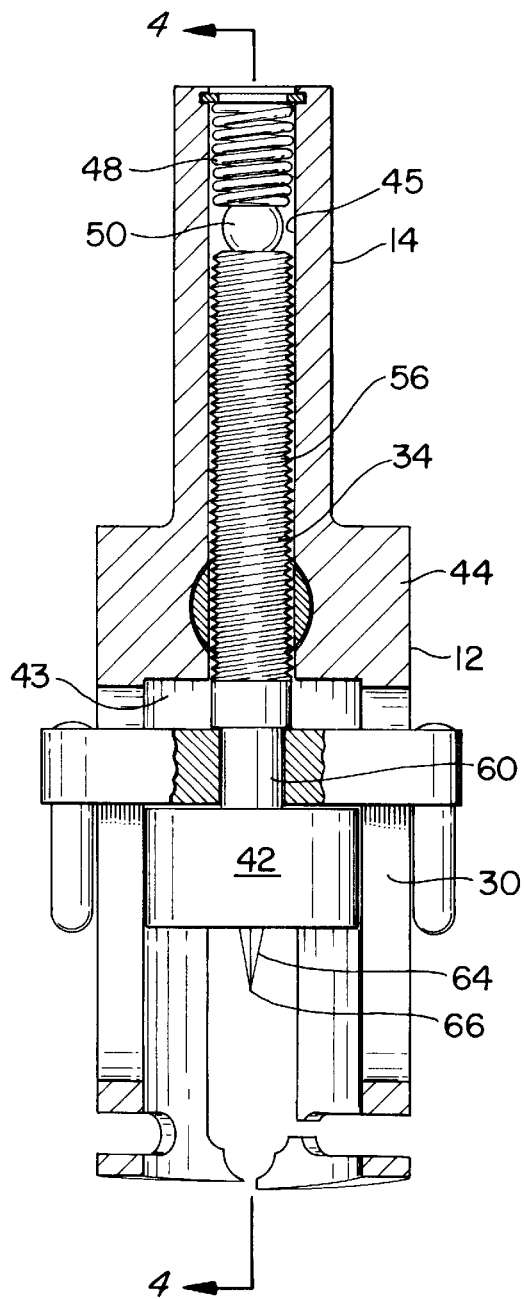
FIG. 3 is a sectional view taken through the vertical center of the perforator of FIG. 1 with the drill bit being retracted.
Figure 4:
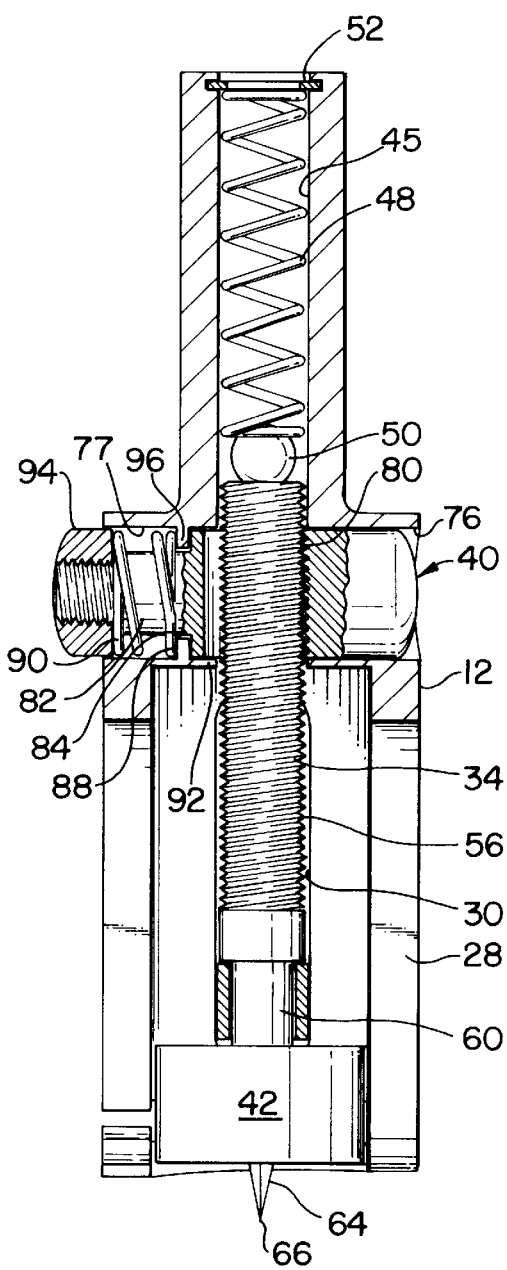
FIG. 4 is a sectional view taken along lines 4—4 of FIG. 3 after the drill bit is deployed in the cutting position.
Figure 10:
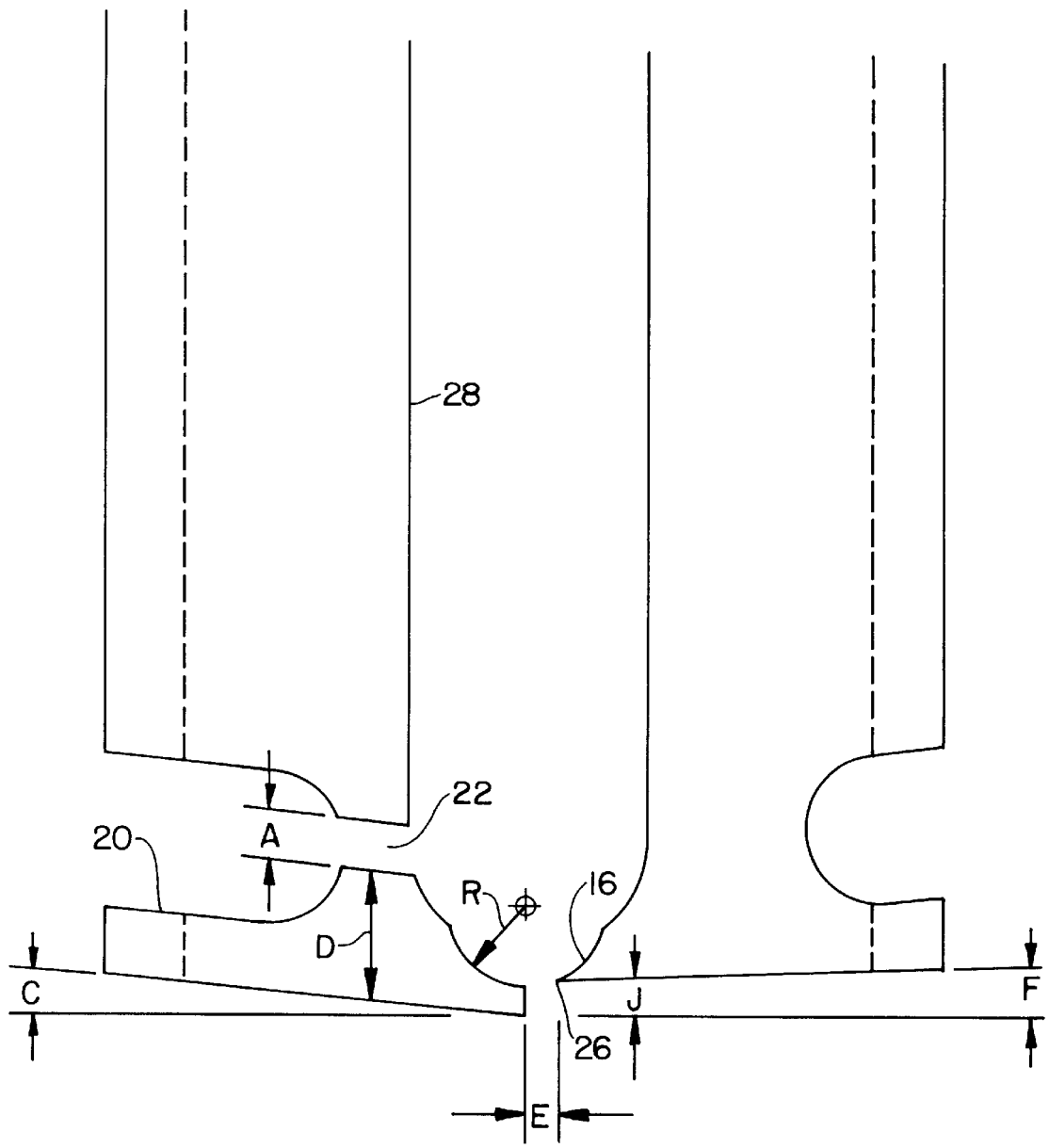
FIG. 10 is a partial an enlarged view in section illustrating the dimensions of the drill bit.
Figure 11:
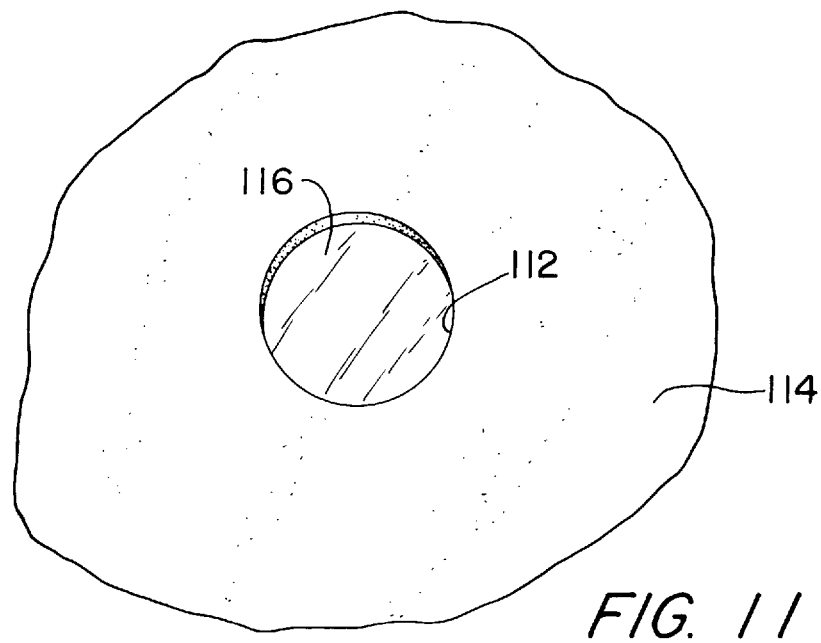
FIG. 11 schematically illustrates a portion of a human skull with the hole drilled and the core cut by the perforator removed.
Figure 12:
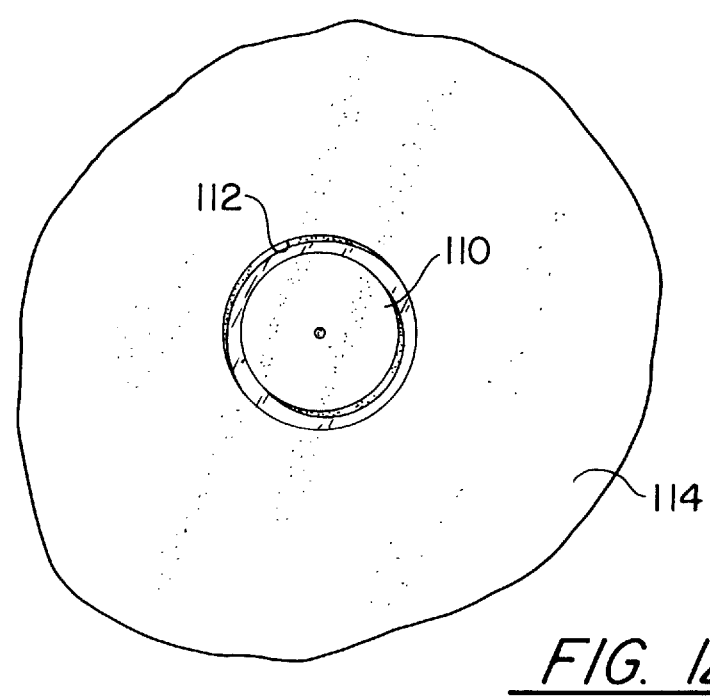
FIG. 12 is a schematic illustration of FIG. 11 with the core or plug portion being inserted back in the drilled hole.
Figure 13:
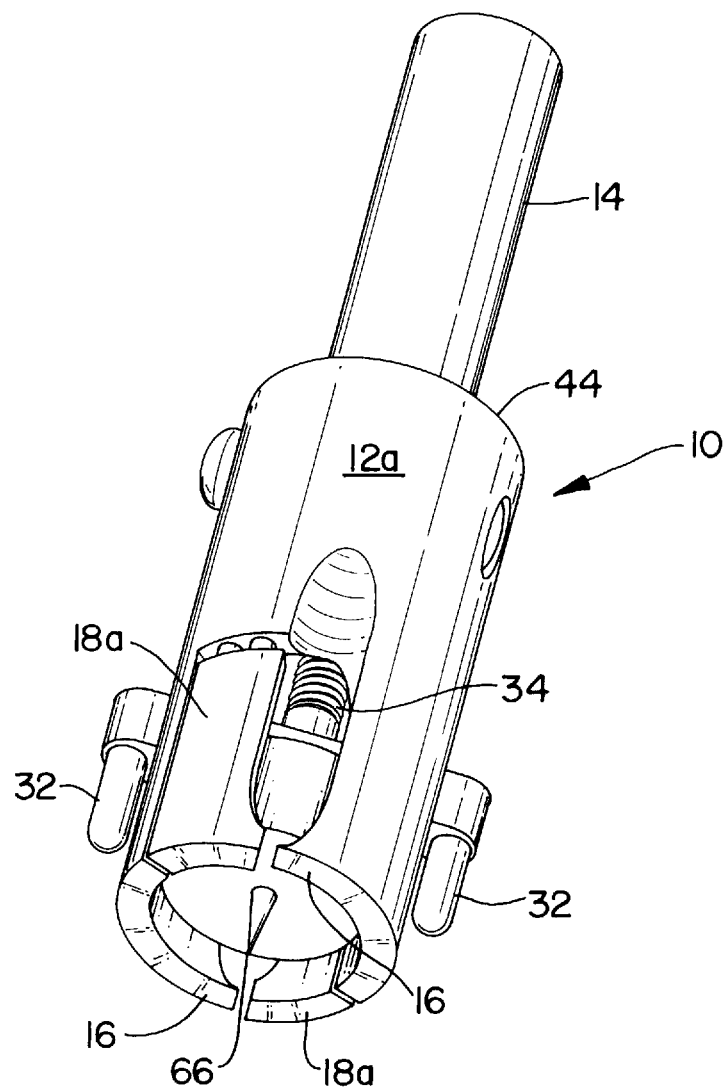
FIG. 13 is a perspective view exemplifying another embodiment of this invention.
Figure 14:
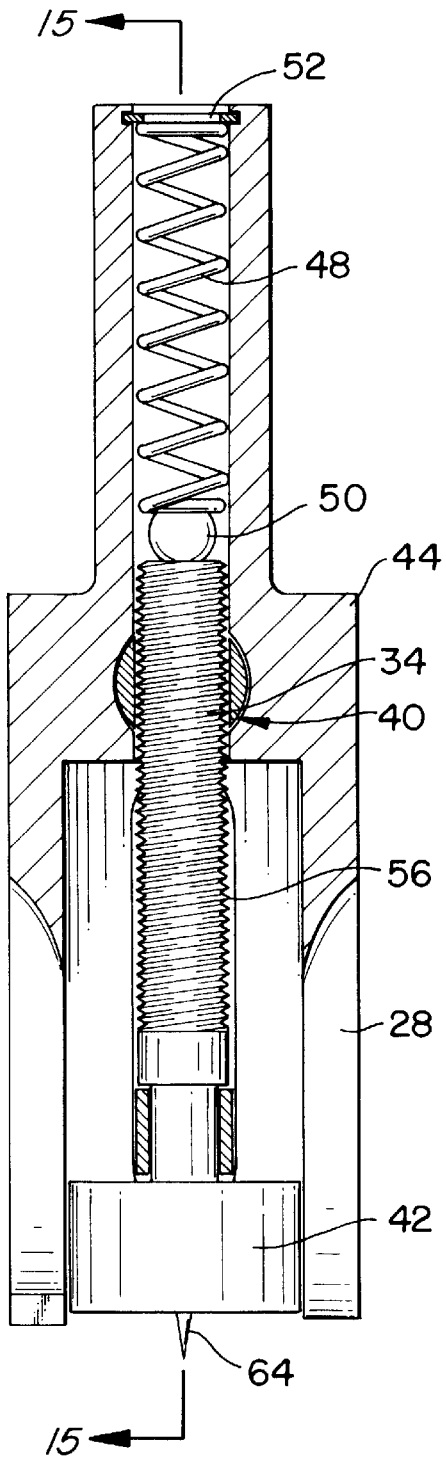
FIG. 14 is a sectional view taken along the vertical central axis of the perforator.
Figure 15:
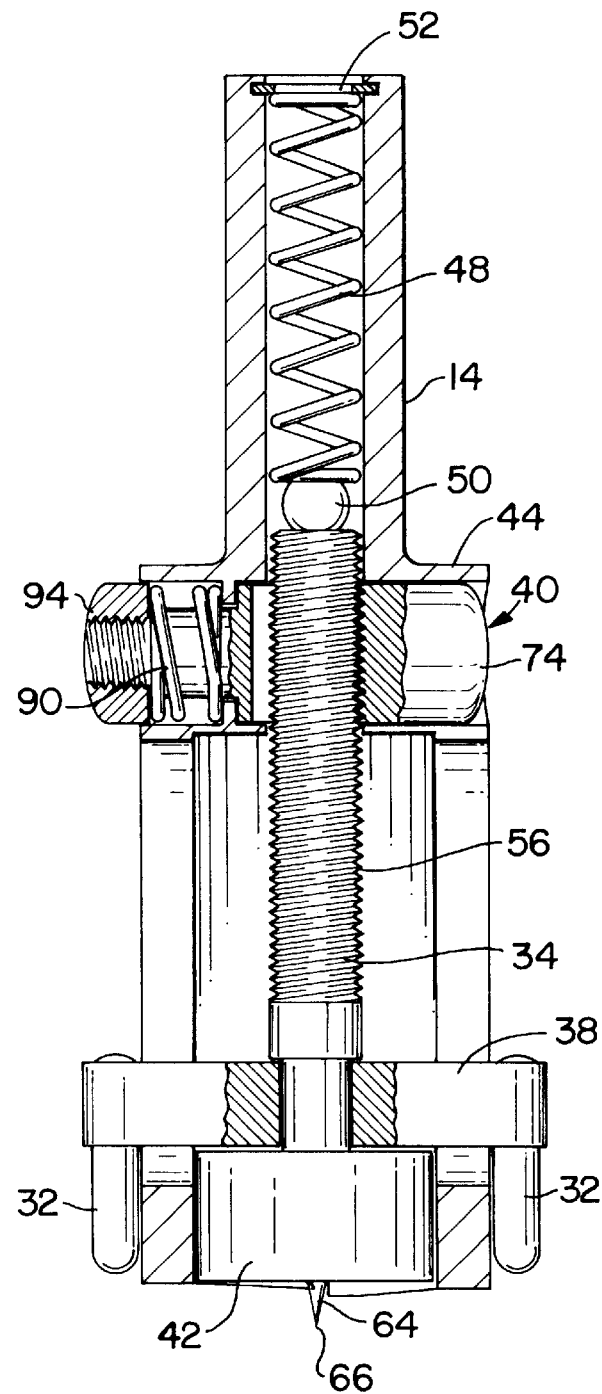
FIG. 15 is a sectional view taken along lines 15—15 of FIG. 14.

The latch 40 serves to either hold the screw in the threaded engagement position or in the retrieved position (FIG. 3) until the protractor is ready for use. When in use the latch is in the normal position where the screw 34 is in engagement as the drilling procedure commences. Latch 40 consists of a plunger element 74 that fits into the lateral bores 76 and 79 formed on diametrically opposed ends of the top portion 44 of drill bit 12. The aperture 78 formed in the latch 40 is dimensioned to lie in the central axis of the drill bit 12 to accommodate the screw 34. As best seen in FIGS. 2 and 4 the latch 40 fits into the drilled bore 76 and the screw 34 is straddled in the oversized hole 78. One end of the hole 78 is formed with threads 80 that complement the threads 56 of screw 34. In manufacturing this element the hole is threaded and the threads on one half of the hole are milled out. It will be appreciated that the hole is sufficiently large to allow the threads 80 to become disengaged with the threads 56. The reduced diameter portion 82 of the latch 40 is dimensioned to fit into the reduced diameter portion 84 of the drill bit 12 and is formed at the junction of the ends of the two bores 76 and 77 (see FIG. 4). This reduced diameter bore 84 defines the annular flange 86 which forms shoulder 88 for retaining coil spring 90 and shoulder 92 that serves as a stop to limit the travel of latch 40. The cap 94 having a threaded bore is threaded to the threaded end 96 of latch 40 securing the assembly in place. The spring 90 is in compression and bears against the end of cap 94 to continuously urge the threads 80 into engagement with the threads 56. To release this engagement the end of cap 94 is depressed to disengage the threads 80 from the screw threads 56 which allows the operator to position the screw 34 in the retracted position and to deploy the screw 34 from the retracted position to start the drilling procedure. The retracted position primarily occurs after the first operation and must be retracted in order to be reused.

As mentioned in the above paragraphs, the invention utilizes a safety mechanism to assure that the drill bit will not penetrate past the bottom of the bone structure a predetermined amount. This safety mechanism consists of the two stop pins 32 and the stop bridge 38 and the screw 34 and latch 40 that was just described. The stop pins 32 may be affixed to the stop bridge in any suitable manner such as by welding, brazing, screwing or they may be formed integrally therewith, noting that they are disposed adjacent the exterior of the drill bit 34. It being understood that the stop pins 32 and bridge 38 act as a unitary member. The diameter of the central straight-through bore 96 of bridge 38 is dimensioned slightly larger than the diameter of the shank portion 60 of the screw 34 so that the bridge 38 and stop pins 32 rotate relative to the screw 34. The width of the bridge 38 is dimensioned to fit into the diametrically disposed slots 30 so that bridge 38 can translate vertically therein and rotate therewith. Slots 30 serve as a guide for the bridge 38 and rotary drive mechanism to rotate the bridge 38 and stop pins 32. The screw 34 fits through the bore 96 of the bridge 38 and the bridge 38 is trapped between the shoulder 62 of screw 34 and the top surface of center driver 42.

From the foregoing it is apparent that the bridge 38 and stop pins 32 rotate with the drill bit 12 and relative to the screw 34 so that as the drill bit penetrates the bone structure and since the latch 40 is threadably secured to the screw 34, the stop pins 32 and bridge 38 remain in the same relative position with respect to the exterior surface of the bone structure and the drill bit 12 will move axially into the drilled hole. Threads 80 of the latch 40 are held into engagement with the threads 56. Obviously, the distance that the ends of stop pins 32 are displaced from the exterior of the bone structure (gap) will be predicated on the length of the stop pins 32 and the relationship of bridge 38 to shoulder 62.

OPERATION OF THE PERFORATOR

In operation, the shaft 14 is inserted into a suitable chuck 100 that is affixed to a suitable commercially available motorized drill 101 and the perforator 10 is located in the position by the surgeon ready to perform the drilling portion of the operation. The perforator is packaged with the threaded screw already in the deployed position where the guide pin is extended beyond the cutting edge of the drill bit. The surgeon at this point is ready to proceed with the operation. The guide pin is placed in the location where the hole is desired and the motor is actuated rotating the drill bit and causing the guide pin to penetrate into the bone and drive the center driver 42 toward the bone structure so that the diamond shaped knurl 72 together with the triangular shape guide pin 64 frictionally hold the screw from rotating. As mentioned above, since the guide pin is in residence with the bone structure and the bottom knurled surface 72 is in contact with the bone structure, the screw 34 will remain stationary and the drill bit 12 will rotate. Also, it will be noted that the stop pins 32 are carried with screw 34 when in the initial deployed position and will be displaced the predetermined 0.03 mil. gap between the end of stops 36 and the outer surface of the bone structure 114 as described above (FIG. 5). With the perforator 10 in the operating condition, the surgeon will then apply pressure to the perforator to force it downwardly which causes the shield to deflect and move axially upwardly exposing the sharp edge 26 of the cutting edge 16 as seen in FIG. 6. Further pressure by the surgeon will expose the cutting edge 16 even further. The exposure of the cutting edge is predicated by the gap 22 where the shield 18 is limited by the projection 106 on drill bit 12 and projection 107 on the top surface of the shield 18. As the drill bit 12 progresses into the bone structure the core or plug of the bone structure will either migrate into the hollow recess 43 and be captured thereby or it will remain in the bone structure. When the drill bit reaches the depth of the drilled hole at the bottom edge of the bone structure, the resistive force will cease and the shield 18 will automatically return to the original position covering the cutting edge 16 and preventing it from doing any further cutting. As long as the drill bit is rotating the stop pins 32 will rotate but will remain the distance of the 0.03 mil gap. It will be appreciated that as soon as the plug 110 separates from the bone structure, the screw 34 will also rotate with the drill bit 12 and obviously, the drill bit 12 can no longer advance relative to the screw. The screw 34 carrying the bridge 38 and stop pins 32 and drill bit 12 will move as a single unit. Should the surgeon apply additional force the perforator 10 and stop pins 32 will displace axially the 0.03 mil. Obviously, additional downward force applied to the perforator will cause the entire unit to travel downwardly causing the stop pins 32 to bear against the top surface of the bone structure preventing further penetration of the drill bit. It is therefore apparent that the perforator will not penetrate the cranial passage to come into contact with the dura 116 and the brain 118. After the perforator is removed, the plug 110 which either falls out on its own initiative or remains captured and if captured it is physically removed by the surgeon. In the instances where it is held in the hole either by the small sliver mentioned above that was observed during the testing or on its own initiative, the removal thereof from the drilled hole may require a special tool or tweezers to pull out the remaining plug. As noted in FIG. 9 plug 110 as shown schematically is then available for use to refill the drilled hole 112 formed in the bone structure 114 as shown schematically in FIG. 10.

While it is contemplated that the drill bit may be disposable it is also contemplated that it can be reused. In this case the threaded screw is now in the retracted position and held by the latch 40. It is deployed by depressing the cap 94. This compresses the spring 90 and positions the latch 40 to the right to release the engagement of the threads 90 and 56. Release of this engagement allows the spring 48 to urge the screw 34 in the downward direction until the tip 66 of guide pin 64 is placed in a position to penetrate into the bone structure. The operation is then repeated as is described above.

Figures 16, 17:
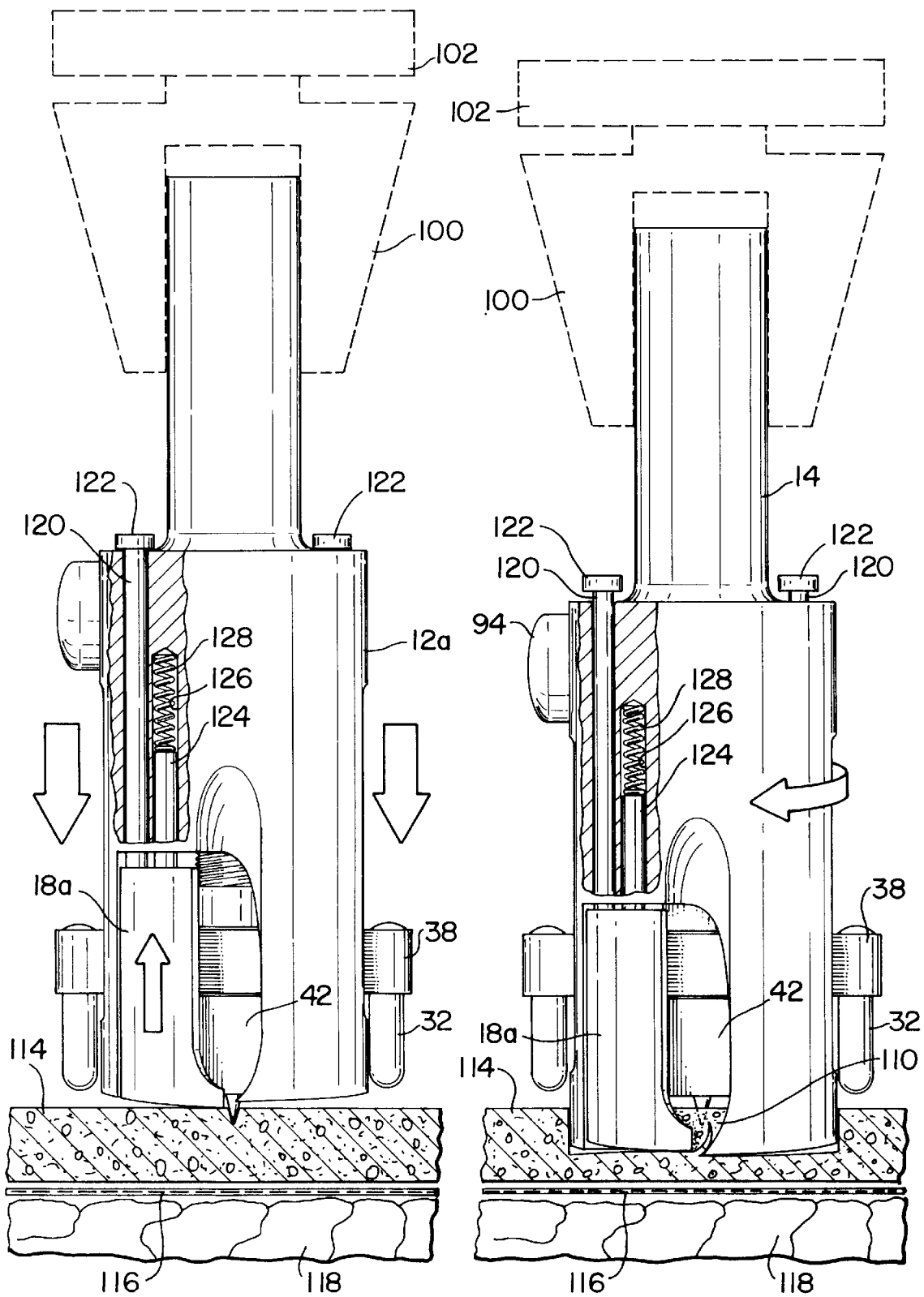
FIG. 16 is a view in elevation illustrating the perforator with the guide pin penetrating the bone surface just prior to the cutting operation of the drill bit.
FIG. 17 is an elevated view identical to the perforator shown in FIG. 16 with the shield retracted and the cutting edge exposed in the cutting operation.

The embodiment exemplified in FIGS. 11 through 22 operate in principle exactly like the embodiment disclosed in FIGS. 1 through 10 except that the perforator is designed with a considerable number of additional components. As best seen in these Figs. the cranial drill or perforator 10 includes a drill bit 12 (like parts in all the Figs. use the same reference numerals), a shaft 14, a cutting edge 16a and a shield 18a. The primary difference between this embodiment and the one disclosed in FIG. 1 is the design of the drill bit 12a and shield 18a. In this embodiment the shield 18a is a separate component that is arcuate in shape and conforms to certain dimensions such as thickness and curvature to define the annular portion of the drill bit. The shield 18a is supported adjacent the cutting edge 16 by the bolt 120 that includes the head 122 that bears against the top surface of the drill bit 12 and is rigidly affixed to the shield 18a. A plunger element 124 fits into an axial recess 126 formed in the top portion 44 of drill bit 12 and is spring loaded by coil spring 128. FIG. 16 shows the shield 18a in the ready-position when no or little resistive load is applied thereto. FIG. 17 illustrates the displacement of shield 18a when it encounters a resistive load and places the cutting edge 16 in the cutting position.

Figure 22:
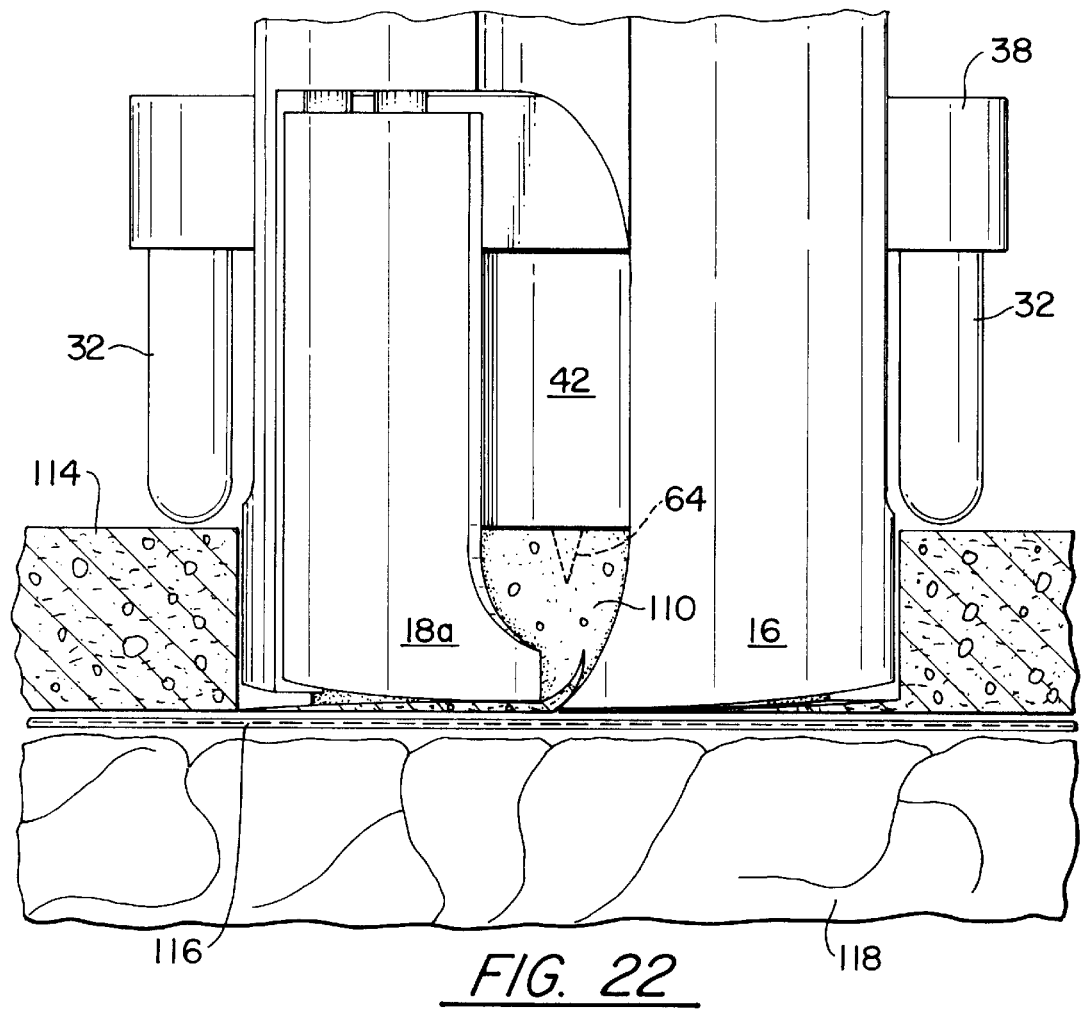
FIG. 22 illustrates the perforator in operation with the cutting edge exposed in the drilling operation.
Figure 23:
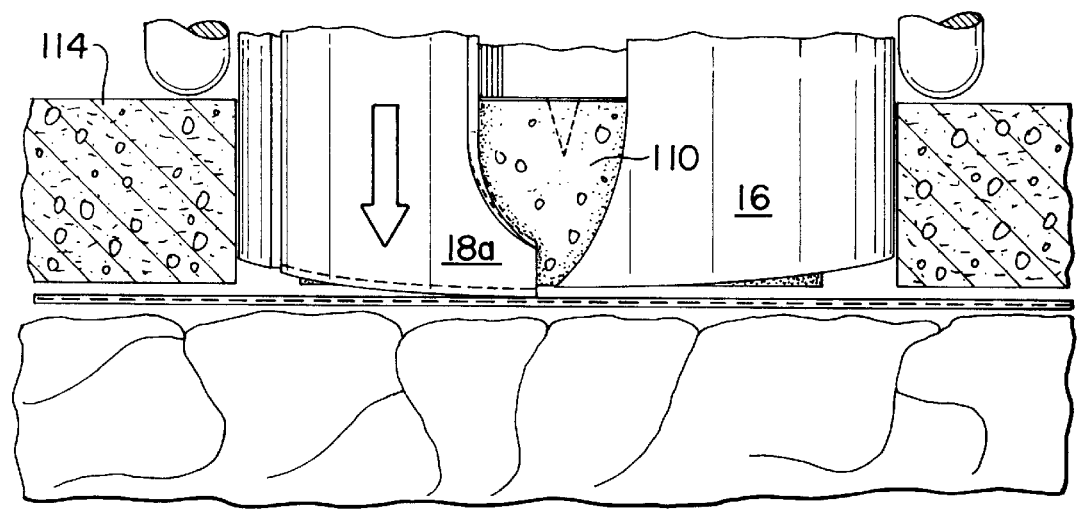
FIG. 23 illustrates the perforator when the load is taken off the shield and it is automatically returned to its original non-cutting position.

The latch 40, screw 34 and stop pins 32 shown in FIGS. 14, 15, 18–20 are identical to and operate the same as they are described in connection with FIGS. 1–6 and for the sake of simplicity and convenience a detailed description thereof is omitted herefrom but is incorporated herein by reference. As shown in FIGS. 22 and 23 when the cutting edge 16 reaches the bottom of the bone structure and depth of the hole being cut is completed, the resistive load ceases so that no load will hold the shield 18a in the up position and it will automatically return to the original position to project below the cutting edge 26 to prevent further cutting. As was described with connection with the operation of the invention described in FIGS. 1–6. The stop pins 32 will prevent penetration into the cranial passage when it comes into contact with the exterior surface of the bone structure 114.

In certain applications it may be desirable to eliminate the sliver from forming on the bone plug. For example, where the drill bit is not parallel to the surface of the bone structure the sliver may rotate in a tilted direction with a potential of contacting the dura. To obviate this problem and as best seen in FIGS. 7 and 7A the side face of the cutting edge 16 is beveled from the bottom edge extending axially upwardly illustrated by reference letter G and extending a short distance along the circumference of the drill bit 12. The corresponding surface of the shield 18 is similarly beveled so that the two surfaces are generally in coincidence with each other during the cutting operation. Tests have shown that this small change in the cutting edge and shield of the drill bit completely eliminates the sliver that heretofore was evidenced on the bottom of the bone plug 110 in some of the prior tests.

In certain application it is desirable to stop rotation of the drill bit at a predetermined point of operation. As for example where the topography of the bottom surface and top surface is drastically different and there are extreme changes in the thickness of the bone, it may be desirable to stop rotation of the drill bit before reaching the bottom of the bone, particularly where in some areas of the drilled hole there is an absence of any bone. In this circumstance it may be desirable to cease cutting as soon as the absence of any bone is attained. To this end this invention includes a declutching mechanism that senses this absence of bone structure and ceases rotation of the drill bit and hence, stops further drilling of the bone structure. The surgeon at this point can break away the bone plug without having to perform an additional drilling. At any event, it leaves open options on how to further proceed to the surgeon.

Figure 24:
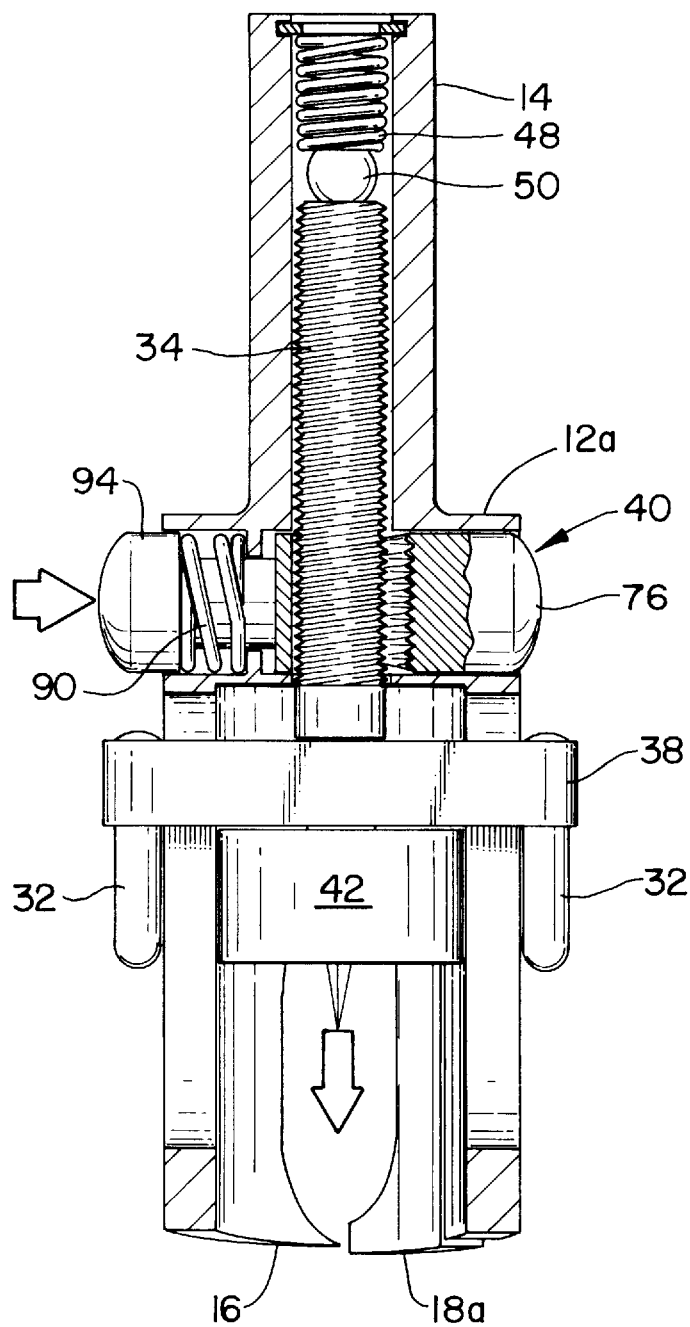
FIG. 24 is an elevated view partly in section and partly full illustrating the perforator with the drill bit positioned in the retracted position.
Figure 25:
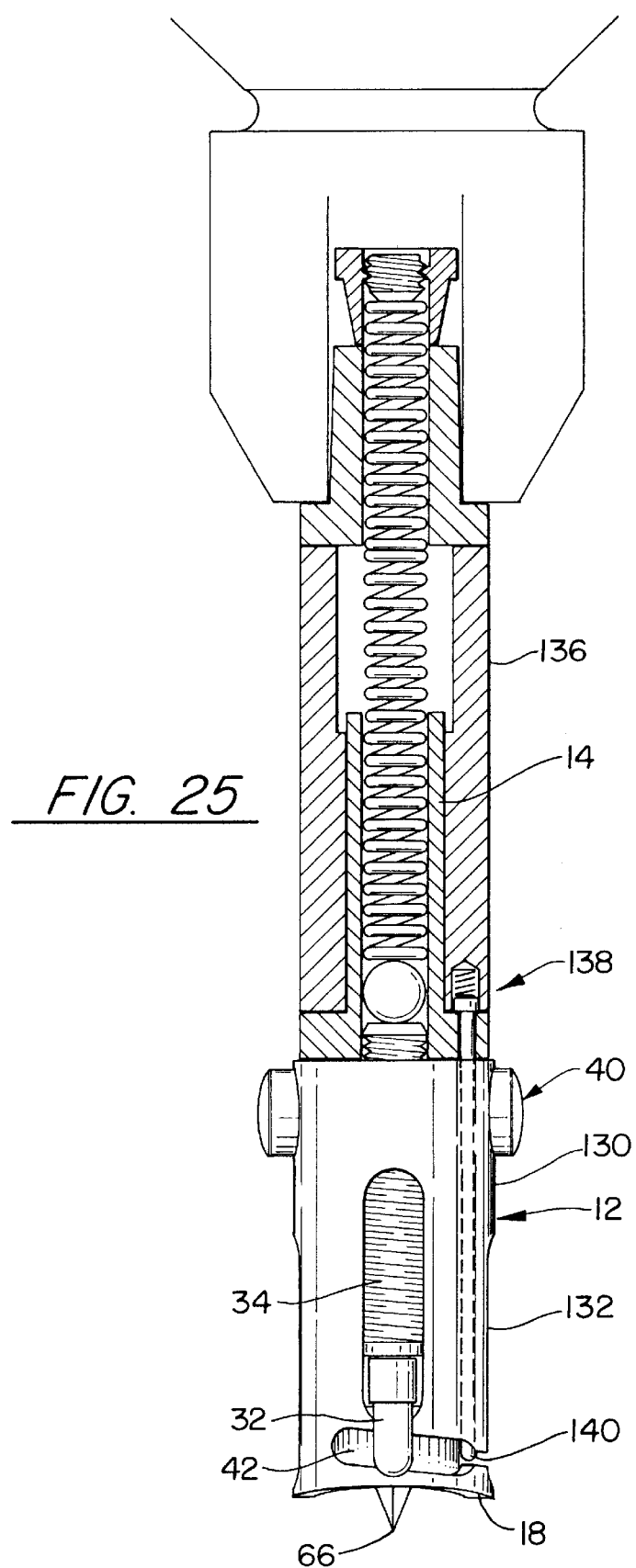
FIG. 25 is a sectional view in elevation exemplifying a clutching mechanism that serves to automatically stop rotation of the drill bit upon sensing a void in the drill passage upon sensing a void in the drilling operation.
Figure 26:
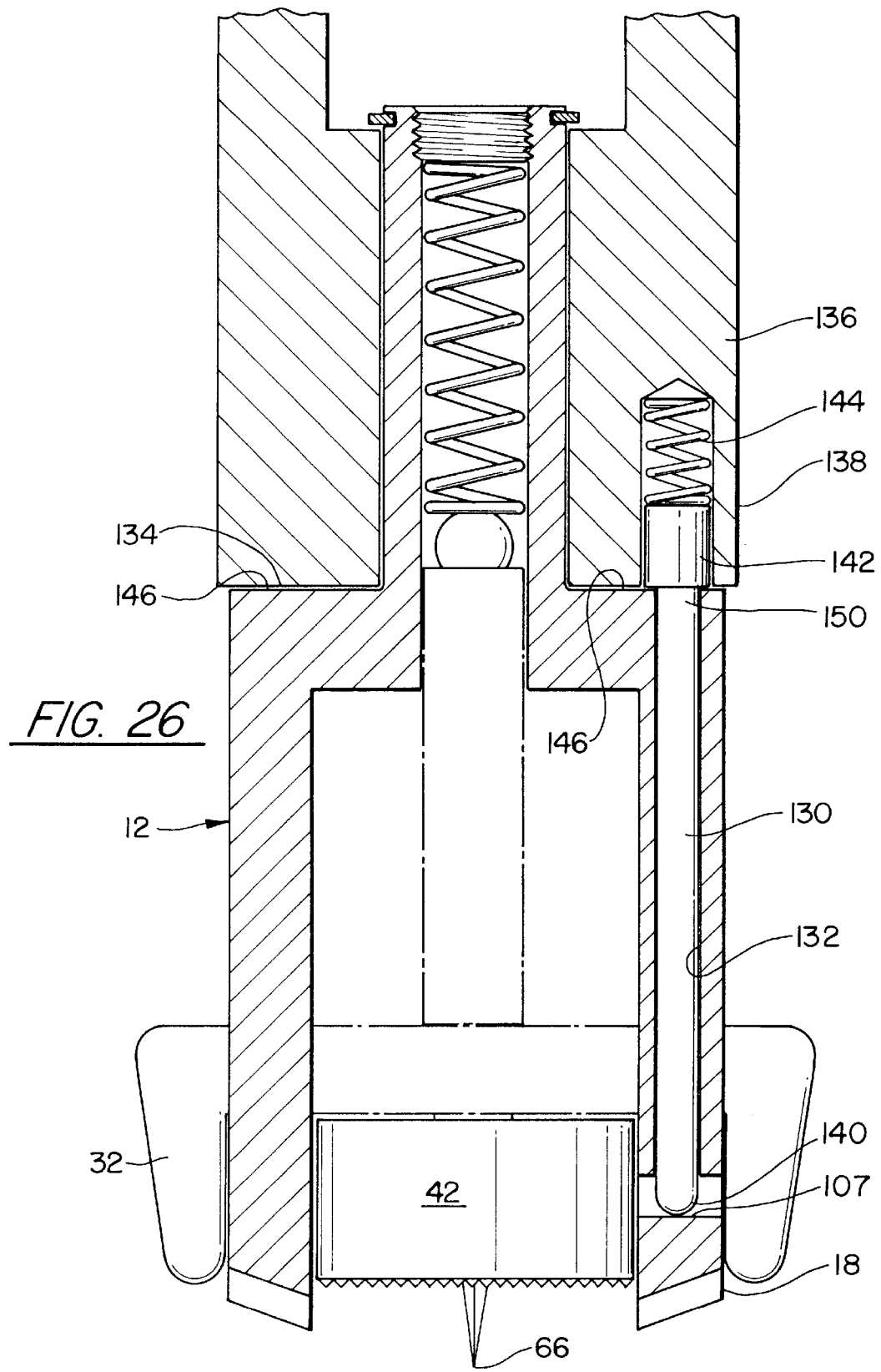
FIG. 26 is an enlarged partial sectional view illustrating the details of the optional clutching mechanism of FIG. 25.

FIGS. 24 and 25 illustrate a declutching mechanism that serves the purpose of ceasing rotation of the drill bit upon sensing a void in the bone structure. As noted in FIGS. 24 and 25 an elongated rod 130 is fitted into the elongated passage 132 formed in drill bit 12 and extends vertically to the top of the radial flange 134. formed on drill bit 12. The shaft 14 (FIG. 1) is modified in this embodiment to accommodate a driver 136 which top portion 138 is formed in the male portion of a commercially available Hudson chuck which in turn is adapted to be fitted to the drill motor. The driver 136 is mounted in rotational movement relative to the stem 14 and hence when in the decoupled mode the stem remains stationary when the clutching mechanism generally indicated by reference numeral 138 is deactivated and the drill motor is in the operative mode.

As noted from the FIGS. 24 and 25, the end portion 140 bears against the projection 107 which is at top portion of the shield 18. The clutching mechanism 138 which consists of plug 142 and coil spring 144 retained in the recess 146 formed on the bottom of driver 136. As noted the diameter of plug 142 is larger than the diameter of the passage 132 so that the bottom surface 146 of plug 142 extends beyond the opening of passage 132 and bears against the top surface 148 of flange 134.

It is apparent from the foregoing that when in the drilling mode the shield 18 is displaced and closes the gap 22 and displaces the rod 130 to move vertically upwardly. The end portion 150 displaces plug 142 and urges it against the load imposed thereon by spring 144. Since the end portion 150 engages the driver 136 which is driven by the drill motor the drill bit will rotate therewith and perform the cutting operation. As soon as the shield senses a void in the hole being drilled it will return to the retracted position and declutch the drill bit from the driver. It is obvious, that the drill bit will stop rotating and cease the drilling operation even though the drill bit has not reached the bottom of the drilled hole.

At this point of the drilling operation, the surgeon can remove the drill bit and since the bone plug 110 (FIG. 14) is still attached to the bone structure, the surgeon with an appropriate tool can remove the bone plug from the partially drilled hole and break loose the remaining attaching bone structure to remove the bone plug.

Although this invention has been shown and described with respect to detailed embodiments thereof, it will be appreciated and understood by those skilled in the art that various changes in form and detail thereof may be made without departing from the spirit and scope of the claimed invention.

We claim:

1. A surgical perforator for drilling a hole in a bone structure, said perforator having a drill bit configured into a hollow cylindrical wall having a bottom end, a cutting edge formed in said wall at said bottom end and lying long the circumference of said cylindrical wall and being in line therewith, a movable shield lying along said circumference and disposed adjacent to said cutting edge, said shield extending at least in line with said cutting edge to prevent said cutting edge from cutting, said shield movable by a resistive force when said perforator is in the drilling mode so as to uncover said cutting edge and said shield automatically returning to its original position when said resistive load ceases, and means for attaching said drill bit to a drill motor to impart rotary motion to said drill bit.

2. A surgical perforator for drilling a hole in a bone structure as claimed in claim 1 wherein said drill bit includes a horizontal slot formed in said wall adjacent to said shield to provide a predetermined gap to allow the automatic displacement of said shield when the resistive load is applied and ceases.

3. A surgical perforator for drilling a hole in a bone structure as claimed in claim 2 including a vertical slot formed in said wall between said cutting edge and said shield wherein said shield cooperates with said cutting edge to permit exposure of said cutting edge when a predetermined resistive load is applied thereto.

4. A surgical perforator for drilling a hole in a bone structure as claim 3 including slots cut into said wall to form said cutting edge.

5. A surgical perforator for drilling a hole in a bone structure as claimed in claim 3 wherein said wall means defines the width of the cut in said bone structure wherein a plug of said bone remains after said cutting operation is completed.

6. A surgical perforator for drilling a hole in a bone structure as claimed in claim 1 wherein said shield is formed from an elongated member having a top, a bottom and opposing sides and configured into an arcuate shape to fit into a recess formed in said wall to form a continuous annular wall, said bottom extending at least a distance to cover said cutting edge, and resilient and flexible means for biasing said shield to cover said cutting edge and permitting said shield to retract when bearing against said bone structure and encountering a predetermined resistive load and automatically retracting to the original position when said resistive load ceases.

7. A surgical perforator for drilling a hole in a bone structure as claimed in claim 6 wherein said resilient and flexible means includes a coil spring inserted into a hole formed in said top and bearing against said wall.

8. A surgical perforator for drilling a hole in a bone structure as claimed in claim 7 wherein said perforator has a central axis, a post having a shank portion and head portion, said shank portion being affixed to said top of said shield and extending through an elongated passage extending through said wall parallel to said central axis and said head extending above said wall for limiting displacement of said shield.

9. A surgical perforator for drilling a hole in a bone structure as claimed in claim 1 including means for preventing said perforator from penetrating into said drilled passage a predetermined amount after said drill bit ceases cutting.

10. A surgical perforator for drilling a hole in a bone structure as claimed in claim 9 wherein said drill bit includes a central axis, said means for preventing penetration includes a threaded screw having an elongated shank threaded at the proximal and distal ends and coaxially disposed relative to said central axis and extending through said drill bit, a center driver threadably supported to said threaded screw at the distal end and having a bottom surface formed with a knurled surface adapted to engage the surface of the bone structure and a centrally disposed guide pin extending from the end of said threaded screw and adapted to penetrate said bone structure, stop pins, a bridge extending through diametrically disposed vertical slots formed in said wall for supporting said stop pins externally of said drill bit, said bridge being supported for rotary motion to said threaded screw between said threaded portions on the distal and proximal end of said threaded screw, and latch means to permit said threaded screw to be positioned by rotating through fixed threads or by rectilinear movement, spring means acting on one end of said threaded to urge said threaded screw to a deployed position, wherein when said threaded screw is in said deployed position said guide pin and knurled surface engage said bone structure to be maintained in a nonrotating condition and said stop pins rotate with said drill bit and moves with said threaded screw to maintain a predetermined distance from the surface of said bone structure as said drill bit penetrates the bone structure, and said threaded screw rotates with said drill bit when said resistive load ceases whereby further penetration of said drill bit will place said stop pins to bear against said bone structure and prevent further penetration of said drill bit.

11. A surgical perforator for drilling a hole in a bone structure as claimed in claim 10 including a latch mechanism having a main body extending through a lateral bore formed in said wall, a straight through passage parallel to said central axis formed in said main body, a portion of said straight through passage having threads formed therein and complementing the threads of said threaded screw and releasable spring means biasing said threads into engagement and the end of said main body being accessible to urge said main body in a direction to disengage said threads, whereby said threaded screw is permitted to be positioned longitudinally by said spring means on the top of said screw.

12. A surgical perforator for drilling a hole in a bone structure as claimed in claim 10 including a shoulder formed between said distal and proximal threaded portions of said threaded screw and said center driver bearing against said shoulder.

13. A cranial perforator for drilling a hole in a bone structure comprising a drill bit configured into a hollow cylindrical wall having a top end, a bottom end, a cutting edge formed in said wall at said bottom end and lying long the circumference of said cylindrical wall and being along line therewith, a movable shield lying in said circumference and disposed adjacent to said cutting edge, said shield extending at least in line with said cutting edge to prevent said cutting edge from cutting, said shield movable by a resistive force when said perforator is in the drilling mode so as to uncover said cutting edge and said shield automatically returning to its original position when said resistive load ceases, and a centrally disposed central shaft extending from said top and adapted to be attached to a chuck of said drill motor to impart rotary motion to said drill bit.

14. A cranial perforator for drilling a hole in a bone structure as claimed in claim 13 wherein said drill bit includes a horizontal slot formed in said wall adjacent to said shield to provide a predetermined gap to allow the automatic displacement of said shield when the resistive load is applied and ceases.

15. A cranial perforator for drilling a hole in a bone structure as claimed in claim 14 including a vertical slot formed in said wall between said cutting edge and said shield wherein said shield cooperates with said cutting edge to permit exposure of said cutting edge when a predetermined resistive load is applied thereto.

16. A cranial perforator for drilling a hole in a bone structure as claim 15 including slots cut into said wall to form said cutting edge.

17. A cranial perforator for drilling a hole in a bone structure as claimed in claim 15 wherein said wall means defines the width of the cut in said bone structure wherein a plug of said bone remains after said cutting operation is completed.

18. A cranial perforator for drilling a hole in a bone structure as claimed in claim 14 including means for preventing said perforator from penetrating into said drilled passage a predetermined amount after said drill bit ceases cutting.

19. A cranial perforator for drilling a hole in a bone structure as claimed in claim 18 wherein said drill bit includes a central axis, said means for preventing penetration includes a threaded screw having an elongated shank threaded at the proximal and distal ends and coaxially disposed relative to said central axis and extending through said drill bit, a center driver threadably supported to said threaded screw at the distal end and having a bottom surface formed with a knurled surface adapted to engage the surface of the bone structure and a centrally disposed guide pin extending from the end of said threaded screw and adapted to penetrate said bone structure, stop pins, a bridge extending through diametrically disposed vertical slots formed in said wall for supporting said stop pins externally of said drill bit, said bridge being supported for rotary motion to said threaded screw between said threaded portions on the distal and proximal end of said threaded screw, and latch means to permit said threaded screw to be positioned by rotating through fixed threads or by rectilinear movement, spring means acting on one end of said threaded to urge said threaded screw to a deployed position, wherein when said threaded screw is in said deployed position said guide pin and knurled surface engage said bone structure to be maintained in a nonrotating condition and said stop pins rotate with said drill bit and moves with said threaded screw to maintain a predetermined distance from the surface of said bone structure as said drill bit penetrates the bone structure, and said threaded screw rotates with said drill bit when said resistive load ceases whereby further penetration of said drill bit will place said stop pins to bear against said bone structure and prevent further penetration of said drill bit.

20. A cranial perforator for drilling a hole in a bone structure as claimed in claim 19 including a latch mechanism having a main body extending through a lateral bore formed in said wall, a straight through passage parallel to said central axis formed in said main body, a portion of said straight through passage having threads formed therein and complementing the threads of said threaded screw and releasable spring means biasing said threads into engagement and the end of said main body being accessible to urge said main body in a direction to disengage said threads, whereby said threaded screw is permitted to be positioned longitudinally by said spring means on the top of said screw.

21. A cranial perforator for drilling a hole in a bone structure as claimed in claim 20 including a shoulder formed between said distal and proximal threaded portions of said threaded screw and said center driver bearing against said shoulder.

22. A cranial drill for drilling a hole in a bone structure comprising a drill bit configured into a hollow cylindrical wall having a closed top, an opened bottom end, a cutting edge formed in said wall at said bottom end and lying along the circumference of said cylindrical wall and being in line therewith, a movable shield lying along said circumference and disposed adjacent to said cutting edge, said shield extending at least in line with said cutting edge to prevent said cutting edge from cutting, said shield movable by a resistive force when said perforator is in the drilling mode so as to uncover said cutting edge and said shield automatically returning to its original position when said resistive load ceases, and a central shaft extending from said top for attaching said drill bit to a drill motor to impart rotary motion to said drill bit.

23. A cranial drill for drilling a hole in a bone structure as claimed in claim 22 wherein said shield is formed from an elongated member having a top, a bottom and opposing sides and configured into an arcuate shape to fit into a recess formed in said wall to form a continuous annular wall, said bottom extending at least a distance to cover said cutting edge, and resilient and flexible means for biasing said shield to cover said cutting edge and permitting said shield to retract when bearing against said bone structure and encountering a predetermined resistive load and automatically retracting to the original position when said resistive load ceases.

24. A cranial drill for drilling a hole in a bone structure as claimed in claim 23 wherein said perforator has a central axis, a post having a shank portion and head portion, said shank portion being affixed to said top of said shield and extending through an elongated passage extending through said wall parallel to said central axis and said head extending above said wall for limiting displacement of said shield.

25. A cranial drill for drilling a hole in a bone structure as claimed in claim 22 including means for preventing said perforator from penetrating into said drilled passage a predetermined amount after said drill bit ceases cutting.

26. A cranial drill for drilling a hole in a bone structure as claimed in claim 25 wherein said drill bit includes a central axis, said means for preventing penetration includes a threaded screw having an elongated shank threaded at the proximal and distal ends and coaxially disposed relative to said central axis and extending through said drill bit, a center driver threadably supported to said threaded screw at the distal end and having a bottom surface formed with a knurled surface adapted to engage the surface of the bone structure and a centrally disposed guide pin extending from the end of said threaded screw and adapted to penetrate said bone structure, stop pins, a bridge extending through diametrically disposed vertical slots formed in said wall for supporting said stop pins externally of said drill bit, said bridge being supported for rotary motion to said threaded screw between said threaded portions on the distal and proximal end of said threaded screw, and latch means to permit said threaded screw to be positioned by rotating through fixed threads or by rectilinear movement, spring means acting on one end of said threaded to urge said threaded screw to a deployed position, wherein when said threaded screw is in said deployed position said guide pin and knurled surface engage said bone structure to be maintained in a nonrotating condition and said stop pins rotate with said drill bit and moves with said threaded screw to maintain a predetermined distance from the surface of said bone structure as said drill bit penetrates the bone structure, and said threaded screw rotates with said drill bit when said resistive load ceases whereby further penetration of said drill bit will place said stop pins to bear against said bone structure and prevent further penetration of said drill bit.

27. A cranial drill for drilling a hole in a bone structure as claimed in claim 26 including a shoulder formed between said distal and proximal threaded portions of said threaded screw and said center driver bearing against said shoulder.

28. A cranial drill for drilling a hole in a bone structure as claimed in claim 27 including a latch mechanism having a main body extending through a lateral bore formed in said wall, a straight through passage parallel to said central axis formed in said main body, a portion of said straight through passage having threads formed therein and complementing the threads of said threaded screw and releasable spring means biasing said threads into engagement and the end of said main body being accessible to urge said main body in a direction to disengage said threads, whereby said threaded screw is permitted to be positioned longitudinally by said spring means on the top of said screw.

29. A surgical perforator for drilling a hole in a bone structure, said perforator having a drill bit configured into a hollow cylindrical wall having a bottom end, a cutting edge formed in said wall at said bottom end and lying along the circumference of said cylindrical wall and being in line therewith, a movable shield lying along said circumference and disposed adjacent to said cutting edge, said shield extending at least in line with said cutting edge to prevent said cutting edge from cutting, said shield movable by a resistive force when said perforator is in the drilling mode so as to uncover said cutting edge and said shield automatically returning to its original position when said resistive load ceases, means for attaching said drill bit to a drill motor to impart rotary motion to said drill bit and clutching means responsive to the movement of said shield to declutch said drill bit from said drill motor.

30. A surgical perforator as claimed in claim 29 wherein said means for attaching the drill bit to said drill motor includes a stem, a driver disposed coaxially relative to said stem and being rotatable relative thereto, said clutch means including a vertical rod disposed in a vertical passage in said drill bit having one end bearing against the top surface of said shield and an opposite end extending to the top surface of said drill bit, said rod being displaced by said shield so that said top end of said rod engages said driver to rotate said driver and couple said drill bit for rotation thereof and to disengage said driver from said drill bit when said shield is retracted upon sensing a void of bone in the drill passage during the drilling operation.

31. A surgical perforator for drilling a hole in a bone structure as claimed in claim 30 wherein said clutch means includes a plug and a spring urging said plug toward said drill bit mounted in a recess formed in said driver and said plug having a larger diameter than the diameter of said vertical passage so that said plug slides over the top surface of said drill bit.

32. A surgical perforator for drilling a hole in a bone structure as claimed in claim 31 wherein said drill bit includes a horizontal slot formed in said wall adjacent to said shield to provide a predetermined gap to allow the automatic displacement of said shield when the resistive load is applied and ceases.

33. A surgical perforator for drilling a hole in a bone structure as claimed in claim 32 including a vertical slot formed in said wall between said cutting edge and said shield wherein said shield cooperates with said cutting edge to permit exposure of said cutting edge when a predetermined resistive load is applied thereto.

34. A surgical perforator for drilling a hole in a bone structure as claim 33 including slots cut into said wall to form said cutting edge.

35. A surgical perforator for drilling a hole in a bone structure as claimed in claim 34 wherein said wall means defines the width of the cut in said bone structure wherein a plug of said bone remains after said cutting operation is completed.

36. A surgical perforator for drilling a hole in a bone structure as claimed in claim 29 including means for preventing said perforator from penetrating into said drilled passage a predetermined amount after said drill bit ceases cutting.

37. A surgical perforator for drilling a hole in a bone structure as claimed in claim 36 wherein said drill bit includes a central axis, said means for preventing penetration includes a threaded screw having an elongated shank threaded at the proximal and distal ends and coaxially disposed relative to said central axis and extending through said drill bit, a center driver threadably supported to said threaded screw at the distal end and having a bottom surface formed with a knurled surface adapted to engage the surface of the bone structure and a centrally disposed guide pin extending from the end of said threaded screw and adapted to penetrate said bone structure, stop pins, a bridge extending through diametrically disposed vertical slots formed in said wall for supporting said stop pins externally of said drill bit, said bridge being supported for rotary motion to said threaded screw between said threaded portions on the distal and proximal end of said threaded screw, and latch means to permit said threaded screw to be positioned by rotating through fixed threads or by rectilinear movement, spring means acting on one end of said threaded to urge said threaded screw to a deployed position, wherein when said threaded screw is in said deployed position said guide pin and knurled surface engage said bone structure to be maintained in a nonrotating condition and said stop pins rotate with said drill bit and moves with said threaded screw to maintain a predetermined distance from the surface of said bone structure as said drill bit penetrates the bone structure, and said threaded screw rotates with said drill bit when said resistive load ceases whereby further penetration of said drill bit will place said stop pins to bear against said bone structure and prevent further penetration of said drill bit.

38. A surgical perforator for drilling a hole in a bone structure as claimed in claim 37 including a latch mechanism having a main body extending through a lateral bore formed in said wall, a straight through passage parallel to said central axis formed in said main body, a portion of said straight through passage having threads formed therein and complementing the threads of said threaded screw and releasable spring means biasing said threads into engagement and the end of said main body being accessible to urge said main body in a direction to disengage said threads, whereby said threaded screw is permitted to be positioned longitudinally by said spring means on the top of said screw.

39. A surgical perforator for drilling a hole in a bone structure as claimed in claim 38 including a shoulder formed between said distal and proximal threaded portions of said threaded screw and said center driver bearing against said shoulder.

* * * * *